US007029465B2

(12) United States Patent
Heyes et al.

(10) Patent No.: US 7,029,465 B2

(45) Date of Patent: Apr. 18, 2006

(54) FILTER AMPOULE SYSTEM

(75) Inventors: Robert H. Heyes, Dalkeith (AU); Peter N. Carpenter, South Perth (AU); Remo Ponta, Wilson (AU)

(73) Assignee: Pharmacia Corporation, Peapack, NJ (US)

( * ) Notice: Subject to any disclaimer, the term of this patent is extended or adjusted under 35 U.S.C. 154(b) by 377 days.

(21) Appl. No.: 10/411,555

(22) Filed: Apr. 10, 2003

(65) Prior Publication Data

US 2004/0010242 A1 Jan. 15, 2004

Related U.S. Application Data

(60) Provisional application No. 60/371,823, filed on Apr. 11, 2002.

(51) Int. Cl.

*A61B 19/00* (2006.01)
*A61M 11/00* (2006.01)
*A61M 37/00* (2006.01)
*B01D 27/00* (2006.01)
*B67D 5/58* (2006.01)

(52) U.S. Cl. .......................... 604/406; 604/24; 604/45; 128/200.14; 210/435; 210/413.1; 222/189.06

(58) Field of Classification Search ................ 604/405, 604/406, 403, 416, 24, 27, 30, 45; 210/435, 210/439, 437, 445, 446, 453, 416.1, 418; 128/200.13, 200.14, 200.21, 203.12, 203.15, 128/203.22, 207.18; 215/DIG. 3, DIG. 8, 215/247, 248, 200, 307, 308, 309, 310–315; 222/92–94, 630–633, 189.06, 129, 135, 145.1, 222/145.7, 145.8, 544, 545

See application file for complete search history.

(56) References Cited

U.S. PATENT DOCUMENTS

| | | | | |
|---|---|---|---|---|
| 2,879,207 | A * | 3/1959 | Poitras | 435/287.7 |
| 3,592,245 | A | 7/1971 | Schneller et al. | 141/25 |
| 4,076,027 | A | 2/1978 | Koenig | 128/272 |
| 4,265,242 | A * | 5/1981 | Cohen | 604/406 |
| 5,002,048 | A | 3/1991 | Makiej, Jr. | 128/200.23 |
| 5,139,031 | A * | 8/1992 | Guirguis | 600/584 |
| 5,433,191 | A * | 7/1995 | Haber et al. | 128/200.14 |
| 5,451,374 | A | 9/1995 | Molina | 422/99 |
| 5,487,737 | A | 1/1996 | Meyer | 604/403 |
| 5,976,824 | A * | 11/1999 | Gordon | 435/29 |
| 6,021,776 | A * | 2/2000 | Allred et al. | 128/200.21 |
| 6,162,648 | A * | 12/2000 | Maloney et al. | 436/178 |

FOREIGN PATENT DOCUMENTS

| | | |
|---|---|---|
| EP | 0 891 712 | 1/1999 |
| WO | WO 01/10486 | 2/2001 |

* cited by examiner

*Primary Examiner*—Patricia Bianco
*Assistant Examiner*—Leslie R. Deak
(74) *Attorney, Agent, or Firm*—Karen B. King; Charles W. Ashbrook

(57) ABSTRACT

The present invention presents a novel ampoule filtration system, and novel methods and devices for using the system to deliver multi-doses of a sterile solution of a therapeutic agent to a subject. The ampoule filtration system includes a sterile filter cartridge attached to the mouth of an ampoule, such that liquid dispensed from the ampoule is drawn through the cartridge, and a means for sealingly engaging the filtration system to a delivery device.

15 Claims, 3 Drawing Sheets

FILTER AMPOULE SYSTEM

CROSS-REFERENCE TO RELATED APPLICATIONS

The present application claims the benefit of U.S. Provisional Application Ser. No. 60/371,823, filed Apr. 11, 2002.

FIELD OF THE INVENTION

The present invention relates to liquid containers designed for delivery of a sterile solution. Particularly, the present invention relates to liquid delivery devices that include a sterile filter cartridge connected to the mouth of an ampoule, such that liquid dispensed from the ampoule is drawn through the cartridge, more particularly, devices that permit withdrawal of multiple doses from an ampoule containing a sterile liquid. Even more particularly, the present invention relates to liquid delivery devices which include a filter cartridge with luer connecter. The present invention also relates to methods of use of such devices to deliver a therapeutic agent to a subject.

BACKGROUND OF THE INVENTION

Ampoules have been used to contain solutions, particularly, active agents such as drugs, for many years. Such ampoules have typically been designed to avoid contamination of or to maintain the sterility of solutions stored therein. For example, some ampoules have been made of glass that is sealed shut after a solution is placed therein. In order to access the solution inside, a top part of the ampoule is cut open, sometimes causing small bits of glass to fall into the interior of the ampoule.

Other ampoules are made of glass or plastic with an opening sealed by a stopper after a solution is placed in the ampoule. The stopper is designed to be punctured by a needle or other sharp object, so that the solution contained in the ampoule can be drawn therefrom. The force required to pierce the stopper often causes users to accidentally strike themselves with the sharp object used, causing abrasions or even deep puncture wounds.

U.S. Pat. No. 5,451,344 by Roger Molina discloses an ampoule stopper designed to avoid the dangers of puncturing, described briefly above. The '344 patent discloses a stopper designed to fit the opening in an ampoule or other vessel, with an opening in the stopper extending from the interior of the ampoule to the exterior, through a male luer connection, complimentary to a connection on a cap. This makes the contents of an ampoule fitted with the modified stopper easily removable. However, it also increases the risk of contamination of the contents of the ampoule.

Filtration systems have been designed to filter solutions from ampoules and other types of containers. For example, U.S. Pat. No. 4,076,027 by Elmer Koenig, discloses a device designed to receive a glass ampoule of the first type described above, after the top of the ampoule has been removed to create an opening through which solution contained therein can be accessed. The device includes a chamber of flexible plastic for receiving the ampoule in an upright position with the opening in the ampoule at the top. The device further includes a filter positioned above the opening in the ampoule, and a body with a cylindrical upper end surrounding the filter, configured to receive a female luer tapered connection. The filter is designed to remove particles of glass from the solution, as a solution is drawn out of the ampoule through the filter and luer connection. This device is clearly only designed to accommodate glass ampoules designed to be broken to access material contained therein, and to filter glass particles therefrom. It is not designed to sterilize solutions as they are removed from an ampoule, nor to prevent contamination of the contents of an ampoule, once it is opened.

Accordingly, what is needed is a container system for a solution that enables multiple doses of the solution to be administered in a sterile form, without contamination.

SUMMARY OF THE INVENTION

The present invention provides devices and methods for containing and delivering sterile solutions, preferably a sterile solution containing at least one therapeutic agent.

One embodiment of the invention is a filter ampoule system, comprising an ampoule with a top end having a mouth with an inner surface defining an opening, and a filter cartridge having a first side comprising a protrusion defining an input channel, a second side comprising a connector defining an output channel, and a hollow interior between the first side and the second side containing a sterilizing filter. The protrusion of the first side of the filter cartridge is attached to the mouth of the ampoule, such that the input channel is aligned with the opening, so that fluid contained in the ampoule can be drawn out of the ampoule through the input channel, through the sterilizing filter, and out the output channel.

Another embodiment of the invention is a method of using such a filter ampoule system to deliver a therapeutic agent to a subject, comprising:

(a) providing a container comprising a filter ampoule port extending from an exterior wall of the container, and an interior wall defining a chamber with an outlet and a filter ampoule port channel extending from the chamber through the filter ampoule port;

(b) providing a filter ampoule system, as described above, wherein the filter cartridge comprises a connector designed to sealingly engage the filter ampoule port and the ampoule contains a solution comprising a therapeutic agent;

(c) sealingly attaching the connector of the filter ampoule system to the filter ampoule port; and (d) forcing a first quantity of therapeutic agent out of the ampoule, through the filter cartridge into the chamber through the channel of the filter ampoule port, and out of the chamber through the outlet.

In an alternative embodiment, the delivery device provided in step (a) further comprises (i) a vial port extending from the exterior wall of the container wherein the interior wall of the container defines a vial port channel extending from the chamber through the vial port, wherein the filter ampoule port is between the outlet and the vial port, (ii) a first valve or first pinch-point in the ampoule port channel with a capacity to control introduction of fluids through the filter ampoule port into the chamber, and (iii) a second valve or second pinch-point in the chamber between the vial port and the filter ampoule port with a capacity to prevent the mixture of fluids introduced into the chamber through the filter ampoule port and the vial port. This device is used in an embodiment of the method of the invention, further comprising the steps of:

connecting a vial containing a bacteriostatic solution to the vial port prior to step (d), preferably, with the second valve or second pinch-point closed to prevent back-flow of any of solution, such as a therapeutic agent solution, that flows through the filter ampoule port channel into the chamber; and following the delivery of the therapeutic dose in step (d), forcing a quantity of bacteriostatic solution through the chamber and out the outlet, preferably, with the first valve or first pinch point closed to prevent cross-contamination of therapeutic agent and the bacteriostatic solution.

When another therapeutic dose is to be administered according to the method described immediately above, therapeutic agent is preferably forced out of the ampoule into the chamber immediately prior to administration of the dose to purge the bacteriostatic solution from the flow path to the outlet, preferably, with the second valve or second pinch point closed to stop backflow of the therapeutic agent.

Other embodiments of the present invention include a delivery apparatus such as is used in the embodiments of the method of the invention, as described herein above.

As is demonstrated herein, the filter ampoule system, the delivery apparatus, and methods of using the system and apparatus to deliver liquids, as disclosed herein, enable one to administer one or more required doses of sterile solutions of therapeutic agents to a subject, preferably via a dose regulating device, without any need of the solution being preserved. The filter ampoule system also enables a manufacturer to sell such systems with solutions having any one of a number of different therapeutic agents contained therein, prior to sale. The filter ampoule system and methods of the present invention overcome the problems associated with earlier devices which require breakage of a glass ampoule prior to use, with devices that required manual puncturing of a stopper with a sharp object, and with devices that allowed direct access to ampoule contents, without any intermittent filtering.

DETAILED DESCRIPTION OF THE INVENTION

Figure 1A:
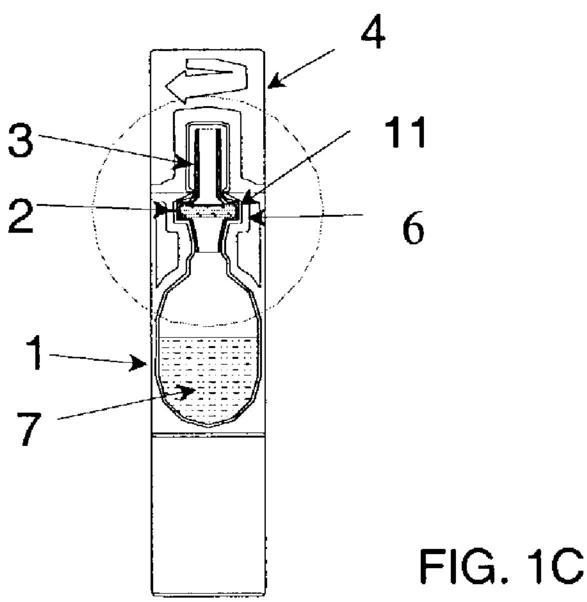
FIGS. 1A and 1B show a cross-section of one embodiment of a filter ampoule system of the present invention, with twist-off cap (4) attached (FIG. 1A) and removed (FIG. 1B).

The term "bacteriostatic solution," as used herein, refers to any solution capable of inhibiting or retarding the growth or multiplication of bacteria.

The term "therapeutic agent," as used herein, refers to a chemical agent that is used in humans for the treatment, prevention, remediation, or cure of a disorder or disease.

The term "dose," as used herein, refers to a carefully measured quantity of a drug that is to be administered to a subject.

The term "vial", as used herein refers to a container of any shape or size designed to hold a solution, such as a bacteriostatic solution, and to dispense the solution into the device of the present solution.

The term "ampoule", as used herein refers to a container of any shape or size designed to hold a solution, such as a therapeutic agent solution, and to dispense the solution through the filter component of the filter ampoule system of the present invention.

The ampoule component of the filter ampoule system of the present invention is suitably of any shape or size. When the filter ampoule system is to be used with a delivery device, as it is in a method of the present invention, then the shape or size of the ampoule is one suitable for use with the device. For example, if the device is a nasal spray delivery device, then the ampoule is preferably sufficiently small to allow the delivery device with filter ampoule system attached thereto to be portable.

The ampoule is suitably made of any malleable material, preferably a malleable synthetic resin, more preferably a malleable form of polyethylene or polypropylene.

The ampoule of the filter ampoule system of the present invention includes a top end and a bottom end, with sides connecting the bottom end to the top end. The top end includes a mouth, with an inner surface defining an opening. The mouth optionally includes a lip protruding from the top end of the ampoule, away from the bottom end.

The filter cartridge of the filter ampoule system includes a first side and a second side. The first side comprises an input channel defined by an opening in the first side. The second side comprises a connector defining an output channel. The connector is preferably configured to form a seal with another connector, such as a port in a therapeutic agent delivery device. The connector is more preferably a male or female type luer connector, even more preferably a male type luer connector. The connector has a proximal end, closest to the second side of the filter cartridge, and a distal end, farthest from the second side of the filter cartridge. The output channel of the connector on the second side is sealingly closed by a cap that is preferably removable by twisting or breaking off.

The first side of the filter cartridge is connected to the ampoule in a way that the input channel is aligned with the opening in the mouth of the ampoule, such that a solution in the ampoule can be drawn therefrom, through the input channel and filter cartridge and out the output channel. Any one of a number of different means is suitable for connecting the filter cartridge to the ampoule, including, but not limited to, a stopper that sealingly engages the inner surface of the mouth of the ampoule with a conduit that sealingly engages the protrusion in the first side of the filter cartridge, a filter cartridge or protrusion in the first side of the filter cartridge that sealingly engages the inner surface of the mouth of the ampoule, a filter cartridge or protrusion in the first side of the filter cartridge that sealingly engages the outer surface of the mouth of the ampoule, and a filter cartridge that is sealingly engaged by the lip of the mouth of the ampoule being in contact with and surrounding at least the perimeter of the second side of the filter cartridge.

When a stopper is used as the connection means, the stopper has an interior surface and an exterior surface, wherein the interior surface is closest to the bottom of the ampoule when the stopper is connected thereto. The stopper also preferably defines a conduit extending from the exterior surface to the interior surface of the stopper, wherein the conduit is adapted for connection, directly or indirectly, to the input channel of the first side of the sterilizing filter. Indirect connection to the input channel is suitably through any one of a number of means known in the art, including but not limited to a needle, a luer connection, and a screw type connection. Direct connection to the stopper is suitably done by adhesion of a portion of the first side of the filter cartridge to the stopper, preferably by insertion of a protrusion from the first side of the filter cartridge sealingly engaging the stopper conduit and allowing access of the contents of the ampoule to the filter. More preferably, the stopper and filter are clamped together onto the ampoule with an aluminium crimp.

When a thermoplastic ampoule is used, the walls of the lip of the ampoule can be moulded to sealingly enclose the filter and can be formed to produce a twist off cap over the filter outlet connector. The cap is designed to twist off at the proximal end of the connector exposing the connector and outlet channel. Such a filtration system can be made by any one of a number of methods, including by the use of Blow-Fill-Seal technology. Alternatively, a break off cap could be incorporated as part of the distal end connector, exposing a luer connection, preferably a male luer connection, when broken off. This alternative is most preferable when using a stopper and crimp connection to the ampoule.

Figure 1B:
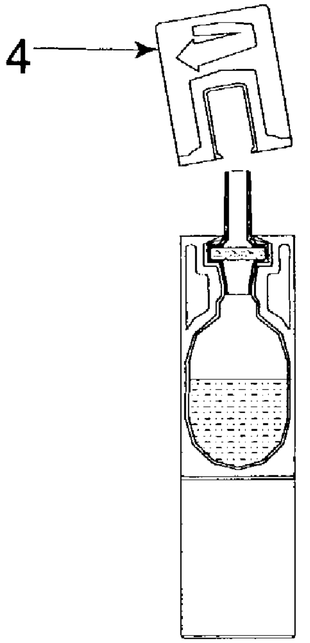

FIGS. 1A and 1B illustrate a cross-section of an embodiment of the filter ampoule system of the present invention. FIG. 1A shows an ampoule (1) with a filter cartridge (2), wherein the filter cartridge (2) includes a luer connector (3) covered by a twist-off top (4). The walls of the ampoule (1) are shown as defining an ampoule mouth (6) and a lip (11), wherein the lip (11) extends over the outer surface of the filter cartridge (2), up to and surrounding the base of the luer connector (3). A therapeutic agent (7) is shown as contained in the ampoule (1). In FIG. 1B, the same filter ampoule system as in FIG. 1A is shown with the twist-off top (4) removed.

Figure 1C:
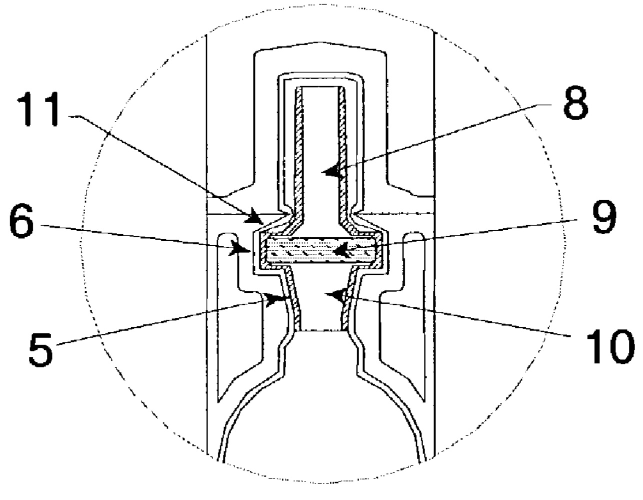
FIG. 1C is a close-up view of a cross section of a region of the filter ampoule system surrounding the filter cartridge (2) of FIG. 1A, a region indicated by a circle in FIG. 1A.

FIG. 1C provides a magnified view of the region of the ampoule system of FIG. 1A indicated by a circle. FIG. 1C illustrates some of the same features of the ampoule system illustrated in FIGS. 1A and 1B, in greater detail. FIG. 1C also illustrates additional features of the filter cartridge (2), including an output channel (8), a sterilizing filter (9), and an input channel (10).

The filter ampoule system illustrated in FIGS. 1A, 1B, and 1C is designed such that when the therapeutic agent (7) is forced out of the ampoule, through the input channel (10), through the sterilizing filter (9), and out the output channel (8), the sterility of the filtered fluid is ensured.

Figure 2A:
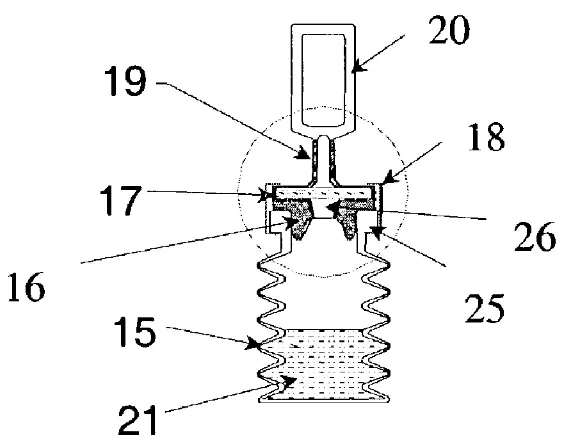
FIGS. 2A and 2B show a cross-section of another embodiment of the filter ampoule system of the present invention, with break-off cap (20) attached (FIG. 2A) and removed (FIG. 2B).
Figure 2B:
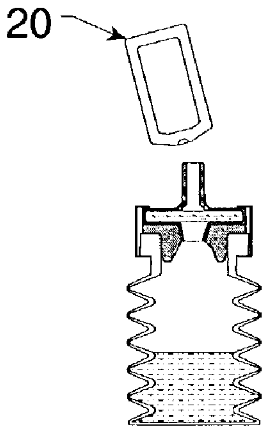
Figure 2C:
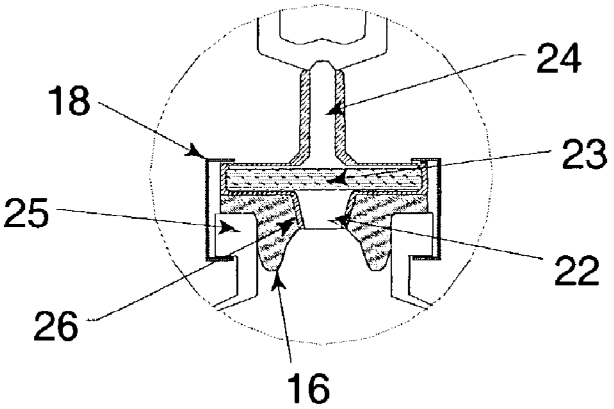
FIG. 2C is a close-up view of a cross section of a region of the filter ampoule system surrounding the filter cartridge (17) of FIG. 2A, a region indicated by a circle in FIG. 2A.

FIGS. 2A and 2B illustrate a cross section of another embodiment of the filter ampoule system of the present invention. In FIGS. 2A and 2C, an ampoule (15) is shown with walls defining a mouth (25), a filter cartridge (17) with a luer connector (19) extending from an outer surface of the filter cartridge (17) and a protrusion (26) extending from the inner surface of the filter cartridge (17). A stopper (16) is shown sealingly engaging the inner surface of the filter cartridge (17), with walls surrounding the protrusion (26) therein. An aluminum crimp (18) is shown pressing the outer surface of the filter cartridge (17) toward the mouth (25) of the ampoule (15), such that the seal between the filter cartridge (17) and the stopper (16) is maintained. The ampoule (15) is shown as containing a fluid (21). The filter ampoule system of FIG. 2A includes a break-off cap (20) that covers the end of the luer connector (19) farthest from the filter cartridge (17). Note that the walls of ampoule (15) are ribbed, like the walls of an accordian, in order to facilitate compression of the ampoule in order to force the fluid out of the filter ampoule system. FIG. 2B shows the same filter ampoule system illustrated in FIG. 2A, after the break-off cap (20) has been snapped off to expose the luer connector (19).

FIG. 2C is a magnified view of the region of the device in FIG. 2A highlighted by a circle. FIG. 2C provides a more detailed view of some of the features of the ampoule system illustrated in FIGS. 2A and 2B, as well as illustrating additional features of the filter cartridge (17) of FIG. 2A, including an output channel (24), a sterilizing filter (23), and an input channel (22).

The filter ampoule system illustrated in FIGS. 2A, 2B, and 2C is designed such that when the fluid (21) is forced out of the ampoule, through the input channel (22), through the sterilizing filter (23), and out the output channel (24), the sterility of the filtered fluid is ensured.

In another embodiment, the present invention is a method of using the filter ampoule system of the present invention to deliver a therapeutic agent, preferably to a dose regulating device. The method of the present invention comprises the steps of providing a delivery device, providing a filter ampoule system containing a therapeutic agent solution, attaching the filter ampoule system to the device, and drawing the therapeutic agent solution out of the ampoule, into and out of the device.

The drug delivery device provided in the method of the present invention includes an interior surface defining a chamber and an exterior surface. The exterior surface defines a filter ampoule port that protrudes away from the remainder of the exterior surface, wherein walls of the filter ampoule port define a first channel extending from the exterior surface to the chamber. The exterior surface also defines a vial port that protrudes away a different part of the remainder of the exterior surface, wherein walls of the vial port define a second channel extending from the exterior surface to the chamber. In addition, the exterior surface defines an outlet.

The distal end of the channel protruding from the second side of the filter cartridge of the filter ampoule system is preferably configured to connect to the filter ampoule port of the delivery device. In a particularly preferred embodiment of the method of the present invention, the connector is in the form of a male luer connector and the filter ampoule port is in the form of a female luer connector or configured to interface with the male luer connector of the filter ampoule system.

Once the filter ampoule system has been connected to the filter ampoule port of the delivery device, removal of a quantity of the therapeutic agent from the ampoule is accomplished by forcing air out of the delivery chamber through the outlet of the delivery device until the therapeutic agent flows out of the ampoule, through the filter, into the chamber, and out the outlet, preferably, by applying pressure to the flexible ampoule.

The method of the present invention preferably further comprises a step of flushing the delivery device chamber with a bacteriostatic solution, to inhibit any potential bacterial growth within the device after delivery of one or more doses of the therapeutic agent. When multiple doses of the therapeutic agent are provided, according to the method of the present invention, the device is preferably flushed with the bacteriostatic solution immediately after the delivery of the dose of therapeutic agent. The chamber would be flushed with therapeutic agent immediately prior to administration of subsequent doses. At each step a valve or pinch point, preferably a one-way valve, would be closed to stop cross-contamination of the bacteriostatic solution and the therapeutic agent. Delivery of the therapeutic agent and control of the flushing steps is preferably controlled by electronic means. A dose regulating device is preferably connected to the outlet.

The bacteriostatic flushing solution is preferably provided to the device through the vial port, after one or more therapeutic agent delivery steps, performed as described above. The bacteriostatic flushing solution is more preferably provided through a vial connected to the vial port, more preferably through a plastic vial connected to the vial port, even more preferably through a plastic vial of polypropylene or polyethylene with a moulded female luer opening. Such vials can be made using any one of a number of known techniques, including but not limited to Blow-Fill-Seal technology.

In a further embodiment, the present invention is the combination filter ampoule system and delivery device described herein-above for use in the methods of delivery of the present invention. This device could be used for any one of a number of means of delivery of various therapeutic agents, preferably to a dose regulating device. When a dose regulating device is used, it is preferably in the form of an oral delivery device or a nasal spray delivery device.

Figure 3:
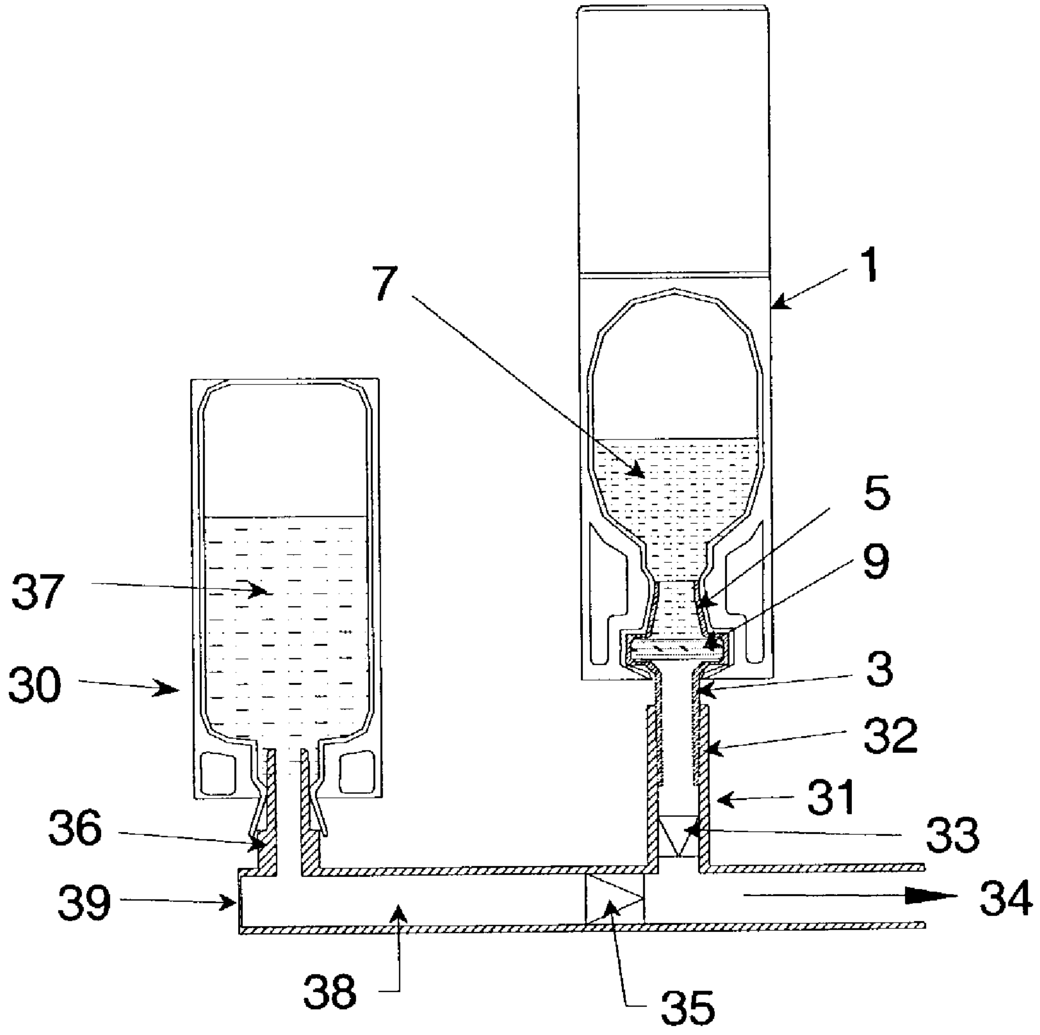
FIG. 3 shows a cross-section of an embodiment of a therapeutic agent delivery device of the present invention.

FIG. 3 illustrates a cross-section of an embodiment of the delivery device of the present invention, described above. FIG. 3 shows a container (39) with walls defining a chamber (38), an outlet (34) at one end, a vial port (36) near an end of the container opposite the outlet (34) protruding from the container and defining an opening extending into the chamber (38), and a filter ampoule port (31) between the vial port (36) and protruding from the container and defining another opening extending into the chamber (38). The container (39) further includes a first valve (33) in the opening in the filter ampoule port (31), and a second valve (35) in the chamber (38) between the filter ampoule port (31) and the vial port (36). The end of the filter ampoule port (31) is in the form of a female luer connector (32). The male luer connector (3) of the filter ampoule system illustrated in FIGS. 1A and 1B is shown attached to the filter ampoule port (31) through the female luer connector (32). The ampoule (1) is shown as containing a therapeutic agent (7). An vial (30) containing a bacteriostatic solution (37) is shown connected to the vial port (36). The first valve (33) and second valve (35) are designed to prevent cross-contamination of the bacteriostatic solution and the therapeutic agent.

The delivery device shown in FIG. 3 is preferably used to dispense a dose of therapeutic agent, according to the following procedure. With the first valve (33) open and the second valve (35) closed, the therapeutic agent is forced through the sterilizing filter (9), into the chamber (38), and out the outlet (34) to a regulating device (not shown). Shortly thereafter, with the first valve (33) closed and the second valve (35) open, bacteriostatic solution (37) from the vial (30) is introduced into the chamber (38) and used to flush the remaining therapeutic agent (7) out the outlet (34).

Although the delivery device illustrated in FIG. 3 is configured with two ports and designed to use two different solutions in practicing the dispensing methods of the present invention, it is contemplated that devices with single or multiple ports designed to accept one or more solutions would be suitable for use in the present invention.

What is claimed is:

1. A method of using a therapeutic agent delivery device filter ampoule system to deliver a therapeutic agent, comprising:

(a) providing a container comprising
- a filter ampoule port extending from an exterior wall of the container,
- an interior wall defining a chamber with an outlet and a channel extending from the chamber through the filter ampoule port,

- a vial port extending from the exterior wall of the container wherein the interior wall of the container defines a vial port channel extending from the chamber through the vial port, wherein the filter ampoule port is between the outlet and the vial port,
- a first valve or first pinch-point in the ampoule port channel with a capacity to control introduction of fluids through the filter ampoule port into the chamber, and
- a second valve or second pinch-point in the chamber between the vial port and the filter ampoule port with a capacity to prevent the mixture of fluids introduced into the chamber through the filter ampoule port and the vial port;

(b) providing a filter ampoule system, comprising
- an ampoule with walls defining a mouth, wherein the ampoule contains a solution comprising a therapeutic agent; and
- a filter cartridge sealingly connected to the mouth of the ampoule, the filter cartridge comprising
  - a first side having a protrusion defining an input channel,
  - a second side having a connector defining an output channel, wherein the connector is designed to sealingly engage the filter ampoule port of the container, and
  - a filter positioned between the first side and the second side, such that when fluid contained in the ampoule is forced out of the ampoule it passes through the input channel, through the filter, and out the output channel, (c) sealingly engaging the connector of the filter ampoule system and the filter ampoule port; and (d) forcing a first quantity of therapeutic agent out of the ampoule, through the filter cartridge into the chamber through the filter ampoule port channel, and out of the chamber through the outlet.

2. The method of claim 1, further comprising repeating steps (b) through (d).

3. The method of claim 1, further comprising:

connecting a vial containing a bacteriostatic solution to the vial port prior to step (d), preferably, with the second valve or second pinch-point closed to prevent back-flow of any of the bacteriostatic solution that flows through the vial port channel into the chamber; and following the delivery of the therapeutic dose in step (d), forcing a quantity of bacteriostatic solution through the chamber and out the outlet, preferably, with the first valve or first pinch point closed to prevent cross-contamination of therapeutic agent and the bacteriostatic solution.

4. The method of claim 1, wherein the connector of the filter ampoule system is a luer connector.

5. The method of claim 4, wherein the connector is a male luer connector, and the filter ampoule system port is in the form of a female luer connector designed to sealingly engage the male luer connector.

6. The method of claim 4, wherein the connector is a female luer connector, and the filter ampoule system port is in the form of a male luer connector designed to sealingly engage the female luer connector.

7. The method of claim 1, wherein the outlet of the delivery device is connected to a dose regulating device, and the method further comprises delivering a dose of the therapeutic agent to a subject.

8. The method of claim 7, wherein the dose regulating device is selected from the group consisting of an oral delivery device and a nasal spray delivery device.

9. The method of claim 7, further comprising administering an additional dose to a subject by forcing a portion of the therapeutic agent out of the ampoule and into the chamber through the filter ampoule port, with the second valve or pinch port closed, immediately prior to administration of the dose in order to purge any bacteriostatic solution remaining in the chamber between the therapeutic agent port and the outlet.

10. A therapeutic agent delivery device comprising a container comprising an interior wall defining a chamber and an outlet from the chamber;

a vial port defining a vial port channel extending from the chamber through the port through an exterior wall;

a filter ampoule system port located between the outlet and the vial port defining a filter ampoule system port channel extending from the chamber through the filter ampoule system port;

a first valve or first pinch-point in the ampoule port channel with a capacity to control introduction of fluids through the filter ampoule port into the chamber, and a second valve or second pinch-point in the chamber between the vial port and the filter ampoule port with a capacity to prevent the mixture of fluids introduced into the chamber through the filter ampoule part and the vial port;

a filter ampoule system, comprising an ampoule with walls defining a mouth, and a filter cartridge sealingly connected to the mouth of the ampoule, the filter cartridge comprising a first side having a protrusion defining an input channel;

a second side having a connector defining an output channel, wherein the connector is designed to sealingly engage the filter ampoule port of the container; and a filter positioned between the first side and the second side, such that when fluid contained in the ampoule is forced out of the ampoule it passes through the input channel, through the filter, and out the output channel; and a ampoule designed to sealingly engage the vial port of the container.

11. The delivery device of claim 10, wherein the ampoule contains a therapeutic agent.

12. The delivery device of claim 10, wherein the ampoule contains a bacteriostatic solution.

13. The delivery device of claim 10, wherein the connector is a luer connector.

14. The delivery device of claim 10, wherein the connector is a male luer connector, and the filter ampoule system port is in the form of a female luer connector designed to sealingly engage the male luer connector.

15. The delivery device of claim 10, wherein the connector is a female luer connector, and the filter ampoule system port is in the form of a male luer connector designed to sealingly engage the female luer connector.

* * * * *